(12) United States Patent
Maier et al.

(10) Patent No.: US 7,557,915 B2
(45) Date of Patent: Jul. 7, 2009

(54) AUTOMATED ACQUISITION OF SPECTRAL DATA AND IMAGE DATA

(75) Inventors: John Maier, Pittsburgh, PA (US);
Patrick Treado, Pittsburgh, PA (US);
Matthew Nelson, Harrison City, PA (US); Lindy McClelland, Pittsburgh, PA (US); Shona Stewart, Pittsburgh, PA (US)

(73) Assignee: ChemImage Corporation, Pittsburgh, PA (US)

( * ) Notice: Subject to any disclaimer, the term of this patent is extended or adjusted under 35 U.S.C. 154(b) by 203 days.

(21) Appl. No.: 11/585,535

(22) Filed: Oct. 24, 2006

(65) Prior Publication Data

US 2007/0133984 A1 Jun. 14, 2007

Related U.S. Application Data

(60) Provisional application No. 60/729,606, filed on Oct. 24, 2005.

(51) Int. Cl.
*G01J 3/44* (2006.01)
(52) U.S. Cl. .............................. 356/301; 356/307
(58) Field of Classification Search ............... 356/301, 356/307
See application file for complete search history.

(56) References Cited

U.S. PATENT DOCUMENTS 5,291,426 A * 3/1994 Collins et al. ............... 356/307
6,717,668 B2 4/2004 Treado et al.
2005/0285023 A1* 12/2005 Liu ............................. 250/221

FOREIGN PATENT DOCUMENTS

| WO | WO 0078217 | 12/2000 |
|---|---|---|
| WO | WO 0225567 | 3/2002 |
| WO | PCT/US2006/041471 | 1/2007 |

OTHER PUBLICATIONS

Matousek et. al. "Fluorescence Suppression in Resonance Raman Spectroscopy using Combined Kerr Gated and SERDS Technique and Automated Spectrum Reconstruction," Central Laser Facility, Annual Report 2001/2002, pp. 185-197. Retrieved on Jun. 4, 2007: <URL: http://www.clf.rl.ac.uk/Reports/2001-2002/pdf/94.pdf>.

* cited by examiner

*Primary Examiner*—Kara E Geisel
(74) *Attorney, Agent, or Firm*—Morgan, Lewis & Bockius LLP (57) ABSTRACT

A system and method to automatically obtain spectra for samples. The method involves a two phase process including a photobleaching phase and a spectral acquisition phase. In the photobleaching phase, a series of spectral data sets of a sample are collected. A relative difference is determined between the background of subsequent spectral data sets is determined and compared to a predetermined threshold value. If threshold difference is less than the relative difference between the background of subsequent spectral data sets, the steps of collecting a series of spectra data sets is automatically repeated. In the spectrum acquisition phase, a series of Raman data sets of the sample are collected until a target SNR is obtained.

28 Claims, 8 Drawing Sheets

FIG. 6

AUTOMATED ACQUISITION OF SPECTRAL DATA AND IMAGE DATA

RELATED APPLICATIONS

This application claims the benefit of U.S. Provisional Application No. 60/729,606 filed Oct. 24, 2005 entitled "Automated Acquisition of Raman Spectral and Image Data" which is incorporated herein by reference in its entirety.

FIELD OF DISCLOSURE

This application relates generally to systems and methods for the automatic collection of Raman spectral and image data.

BACKGROUND

Raman spectroscopy is a powerful technique for rapid, non-invasive and reagentless analysis of materials, including biological cells and tissues. There has long been interest in applying Raman spectroscopy to biological tissues in general and breast cancer samples in particular. Raman spectroscopy and imaging are molecular diagnostic techniques that have demonstrated promise for detection of pathogens. In the area of biothreat detection and identification, Raman spectroscopy provides specific molecular information that is essential for an accurate assessment of potential biothreats. Automation of spectral acquisition is a critical step in the implementation of a new, important class of continuous, on-line detection strategies that will increase reproducibility and speed of biothreat detection.

Acquiring a Raman spectrum involves exciting the vibrational states of molecules using light, and recording light scattered from the molecules during this process. A Raman spectrum indicates the relative intensity of the excitation of molecular vibrations by recording the amount of light scattered from molecules as a function of energy shift from the exciting illumination. The pattern of a Raman spectrum is determined by the structure of the molecule under study and can be used to identify molecular compounds. In a complex molecular system such as an organism, tissue or cell Raman scattering occurs from all of the molecular species in the system and the result is a complex superposition of the spectra from the constituent molecules which is often still specific enough for identification.

In many samples of biological origin, laser illumination leads to luminescence, usually referred to as autofluorescence, in addition to Raman scattering. Spectroscopically this fluorescence leads to a spectrally broad background on top of which the Raman scattering is measured. This autofluorescence will often dissipate after prolonged laser exposure. A common practice is to allow a sample to "photobleach" prior to acquisition in order to increase the Raman scatter-to-background ratio and obtain a high quality Raman spectrum.

An alternative approach to reduce autofluorescence in biological samples is to illuminate with a longer wavelength laser and thus excite less autofluorescence in the sample. This is possible, however using a longer illumination wavelength has limitations of its own. Raman scattering is proportional to $v^4$, where v is the frequency of the illuminating radiation. As the illumination is changed to longer wavelengths or lower frequency, the amount of Raman scattering decreases along with the excited autofluorescence. Raman data collection is typically performed in the visible wavelength range (~400-700 nm) to take advantage of the increased Raman scattering of the sample.

Traditionally, trained spectroscopists decide on acquisition parameters based on their experience and the performance of the instrument and the response of the sample. The spectroscopist determines when a sample is photobleached and then determines the appropriate acquisition parameters (integration time, signal averages etc.) for the desired result. These determinations are based on the spectroscopist's expertise. A more consistent and objective approach is needed to exploit the molecular sensitivity of Raman spectroscopy in applications where users are not trained Raman experts. Automated spectral acquisition is a means of introducing consistency to data acquisition step in any application area.

SUMMARY

The present disclosure provides for a method to automatically obtain spectra for samples A first spectral data set of a sample is collected where the first spectral data set has a corresponding first background data set. A subsequent spectral data set of the sample is automatically collected where the subsequent spectral data set has a corresponding second background data set. A relative difference is determined between the first and second background data sets. A threshold value is compared to the relative difference. The second background data set is designated as the first background dataset and the step above are iteratively repeated until the relative difference is less than the threshold value.

In one embodiment, an initial Raman data set of the sample is collected using an integration time, where the Raman data set has a corresponding signal to noise ratio ("SNR"). A target SNR is compared to the initial SNR. If the target SNR is less than the initial SNR spectral acquisition is concluded and the initial spectrum is reported. If the target SNR is greater than the initial SNR, a subsequent Raman data set of the sample is automatically collected using the integration time where the subsequent Raman data set has a corresponding second SNR. The subsequent Raman data set and the prior Raman data set are averaged to generate an averaged Raman data set having an averaged SNR ratio. The target SNR is compared to the averaged SNR. If the target SNR is greater than the SNR of the averaged spectra, the averaged Raman data set is designated as the initial Raman data set and the steps above are iteratively repeated. If the target SNR is less than or equal to the SNR of the averaged spectrum, the spectrum acquisition phase is concluded and the averaged Raman data set is reported.

In another embodiment, the spectral data set and the subsequent spectral data set are automatically collected at a time interval of less than 5 seconds.

In yet another embodiment, the minimum difference between the corresponding background data set and the corresponding subsequent background data set is less than 5 percent.

In one embodiment, the spectroscopic data set includes a plurality of Raman spectra and a plurality of spatially accurate wavelength resolved Raman images.

The present disclosure further provides for a storage medium containing machine readable program code, which, when executed by a processor, causes the processor to automatically perform a series of steps. A spectroscopic device is configured to: collect a first spectral data set of a sample, said spectral data set having a corresponding background data set; and automatically collect a second spectral data set of said sample, the second spectral data set having a corresponding second background data set. A relative difference is determined between the first and second background data sets. A threshold value is compared to the relative difference. The second background data set is designated as the first background dataset and the steps above are iteratively repeated until the relative difference is less than the threshold value.

In another embodiment, the readable program code causes the processor to further configure the spectroscopic device to collect an initial Raman data set of the sample is collected using an integration time, where the Raman data set has a corresponding signal to noise ratio. A target SNR is compared to the initial SNR. If the target SNR is less than the initial SNR spectral acquisition is concluded and the initial spectrum is reported. If the target SNR is greater than the initial SNR, a subsequent Raman data set of the sample is automatically collected using the integration time where the subsequent Raman data set has a corresponding subsequent SNR. The subsequent Raman data set and the prior Raman data set are averaged to generate an averaged Raman data set having an averaged SNR ratio. The target SNR is compared to the averaged SNR. If the target SNR is greater than the SNR of the averaged spectra, the averaged Raman data set is designated as the initial Raman data set and the above steps are iteratively repeated. If the target SNR is less than or equal to the SNR of the averaged spectrum, the spectrum acquisition phase is concluded and the averaged Raman data set is reported.

The present disclosure further provides for a system including a spectroscopic device, an imaging device, a machine readable program code containing executable program instructions; and a processor operatively coupled to the spectroscopic device and the imaging device and configured to execute the machine readable program code so as to perform a series of steps.

BRIEF DESCRIPTION OF THE DRAWINGS

The accompanying drawings, which are included to provide further understanding of the disclosure and are incorporated in and constitute a part of this specification, illustrate embodiments of the disclosure and, together with the description, serve to explain the principles of the disclosure.

In the drawings.

DESCRIPTION OF THE EMBODIMENTS

Reference will now be made in detail to the embodiments of the present disclosure, examples of which are illustrated in the accompanying drawings. Wherever possible, the same reference numbers will be used throughout the drawings to refer to the same or like parts.

The present disclosure describes methods for the automated acquisition of spectroscopic data as a means of introducing consistency to data acquisition in any application area. In one embodiment, the data acquisition is accomplished in a two phase process. The first phase corresponds to a photobleaching phase where the sample is continuously irradiated. During the photobleaching phase, spectra are automatically and continuously collected, until the autofluorescence of the sample which obscures the detection of the Raman scattering, dissipates. The second phase corresponds to a data acquisition phase where high quality Raman spectra are automatically collected until some user defined measure of spectral quality is reached. In another embodiment, the photobleaching phase and the data collection phase are integrated into a single step.

Figure 1:
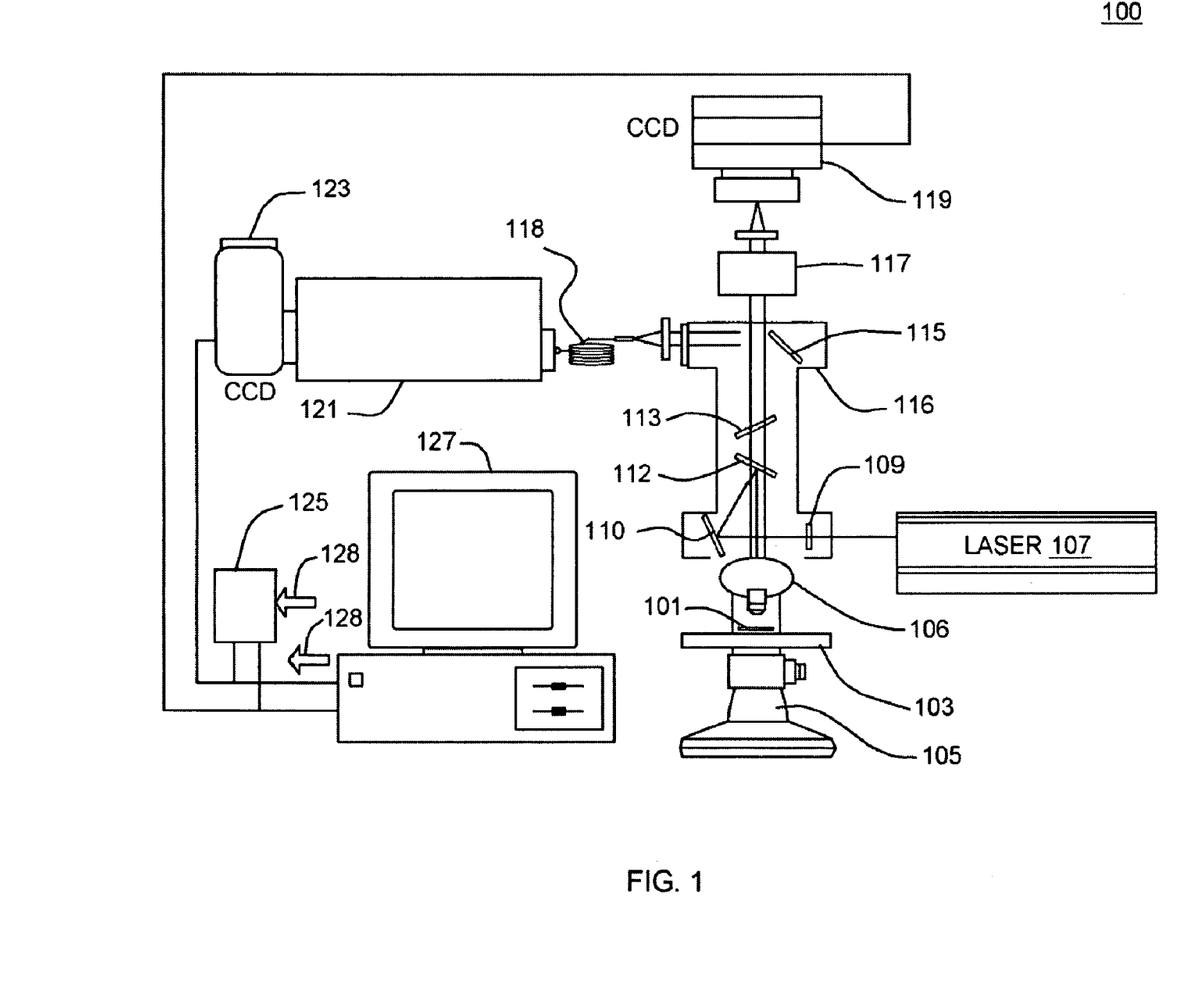
FIG. 1 schematically represents an exemplary system of the present disclosure.

FIG. 1 schematically represents an exemplary system 100 which may be used to perform the methods of the present disclosure. System 100 includes, in a single platform, an imaging device in the form of a microscope objective 106, a spectroscopic device in the form of an imaging spectrometer 117 or a dispersive spectrometer 121, a detector 123, a processor 127, a database 125 and machine readable program code 128. System 100 further includes laser light source 107, white light source 105, bandpass filter 109 to remove $SiO_2$ bands arising from a laser excitation fiber optic. The laser light is directed to a band reject optical filter 110 and propagated through an imaging objective 106 to illuminate the sample 101. Objective 106 collects photons emanating from the sample 101. Notch filters 112 and 113 reject light at the laser wavelength. The machine readable program code contains executable program instructions. Processor 127 is operatively coupled to spectroscopic device 117 or 121 and the imaging device 106. Processor 127 is configured to execute the machine readable program code so as to perform the methods of the present disclosure.

Though the discussion herein focuses on the system illustrated in FIG. 1, the practice of the method of this disclosure is not limited to such a system. An alternative system with the ability to deliver digital images and spectroscopic data sets is described in U.S. Pat. No. 7,046,359 entitled "System and Method for Dynamic Chemical Imaging" which is incorporated herein by reference in its entirety.

The sample includes any sample which generates auto fluorescence upon illumination. Examples of such samples include microorganisms, viruses, biologically derived material including tissue and cells from animals including tissues. Further examples include samples of materials which are part of manufacturing process including polymers, pharmaceuticals or other chemical constituents and mixtures. The method applies equally well to a sample where there is no autofluorescence which changes with laser exposure.

The photobleach phase is designed to mimic the expert spectroscopist's assessment of a stable "photobleached" sample by evaluating the temporal variation of the spectrum in a spectral region where no Raman scatter is present. This is achieved by acquiring relatively rapid sequential spectra. When the relative change of the fluorescence background goes below a predetermined threshold value the photobleach phase is terminated. This allows the acquisition to proceed in the case of a sample which photobleaches more rapidly and can lead to a time savings. The added advantage is that the stability of the fluorescence background is quantitatively determined through this process.

Figure 2:
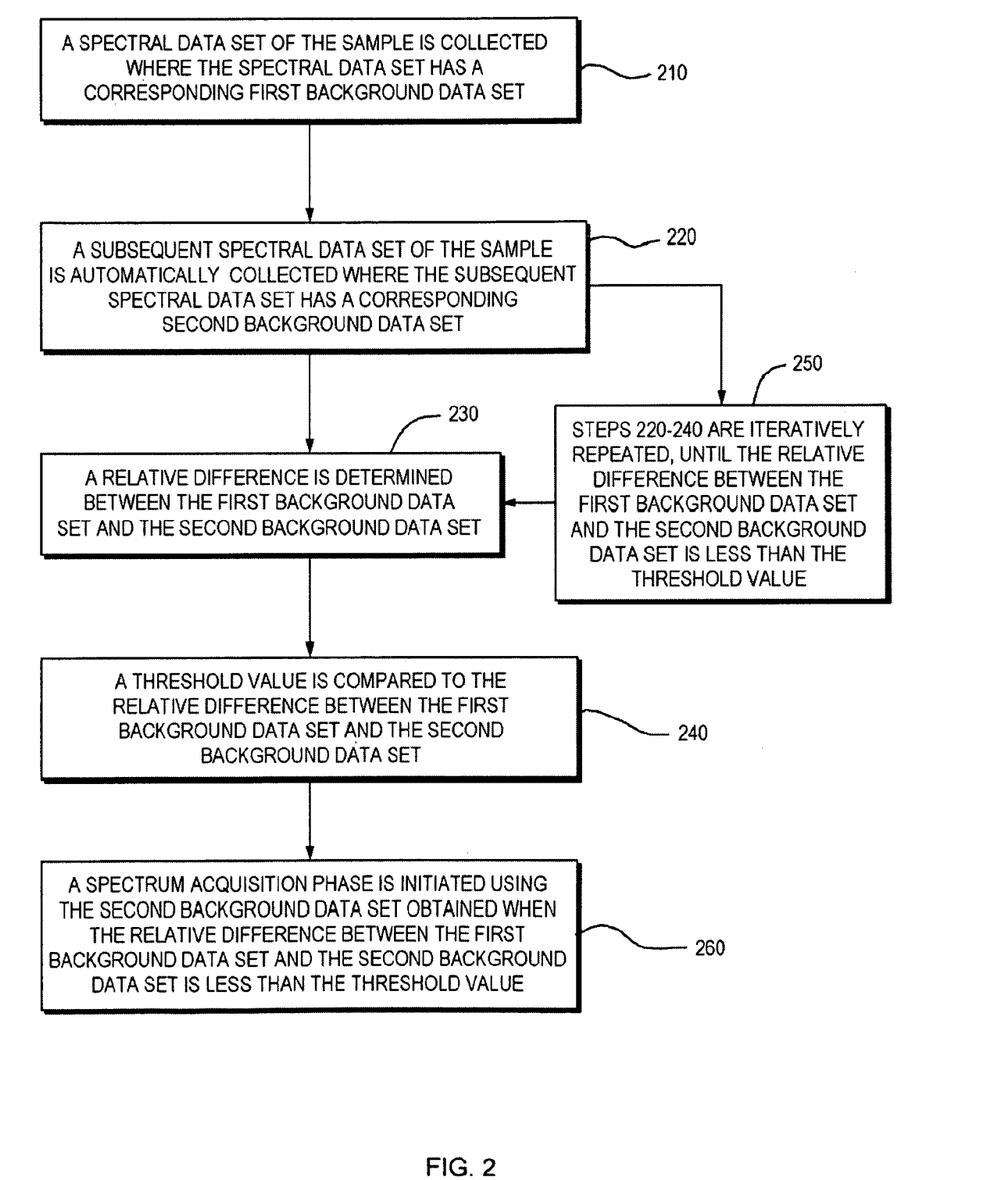
FIG. 2 is a flow diagram illustrating an exemplary method of the present disclosure.

FIG. 2 is a flow chart illustrating the steps of the photobleaching phase. In step 210, a first spectral data set of the sample is collected where the first spectral data set has a corresponding first background data set. In step 220, a second spectral data set of the sample is automatically collected where the second spectral data set has a corresponding second background data set. In one embodiment, the first spectral data set and the second spectral data set are automatically collected at a predetermined time interval. In another embodiment, the predetermined time interval is less than five seconds. In yet another embodiment, the predetermined time interval is one second.

The first spectral data set and the second spectral data set (collectively, "sequential spectral data set") are obtained at a selected wavelength or wavelength range indicating the photodynamic properties of the sample. The sequential spectral data set may include one or more spectra. Each sequential spectral data set includes data collected in a wavelength region of the spectrum corresponding to the spectral background, the background data set. In one embodiment, the one or more spectra include a spectral background region where no Raman scattering is detected. In another embodiment, the one or more spectra include a spectral background region in a wavelength region ranging from 2400 $cm^{-1}$ to 2700 $cm^{-1}$.

In another embodiment, the spectral data set and the subsequent spectral data set may include one or more spatially accurate wavelength resolved images. Each spatially accurate wavelength resolved image includes a background region of interest from which the background data set is obtained. The one or more spatially accurate wavelength resolved images include an image taken at a wavelength corresponding to a region where no Raman scattering is detected. In another embodiment, the one or more spatially accurate wavelength resolved images include an image taken at a wavelength in the region ranging from 2400 $cm^{-1}$ to 2700 $cm^{-1}$.

With further reference to FIG. 2, a relative difference is determined between the first background data of the spectral data set and the second background data set, in step 230. In step 240, a threshold value is compared to the relative difference. In one embodiment, the threshold value is less than five percent. In another embodiment, the threshold value is less than one percent. In step 250, if the threshold value is less than the relative difference between the first background data set and the second background data set, the second background data set is designated as the first background data set. Steps 220-240 are then iteratively repeated until the relative difference is less than the threshold value.

The termination of repeated collection of subsequent spectral data sets may be triggered by various factors. In one embodiment, the repeated collection of subsequent spectral data sets is terminated after repeating steps 220-240 a predetermined number of times. Exemplary numbers of times are 1, 2, 5, 10, or 20 iterations. In another embodiment, an estimation of the ratio between signal data to the background data is used to terminate the repetition of steps 220-240. The signal data is determined from a signal found in a second spectra data set in a wavelength region with Raman scattering. In still another embodiment, if the threshold value is less than or equal to the relative difference between the first background data set and the second background data set, the repetition of steps 220-240 is terminated. In another embodiment, the second background data set, for the spectrum obtained with the relative difference between the first and second background data sets is less than the threshold difference, is used in a spectrum acquisition phase, step 260 of FIG. 2. In this embodiment, a subsequent data set collected during a final iteration of step 220 is used to determine an integration time which is used during the data acquisition phase of the method.

Figure 3:
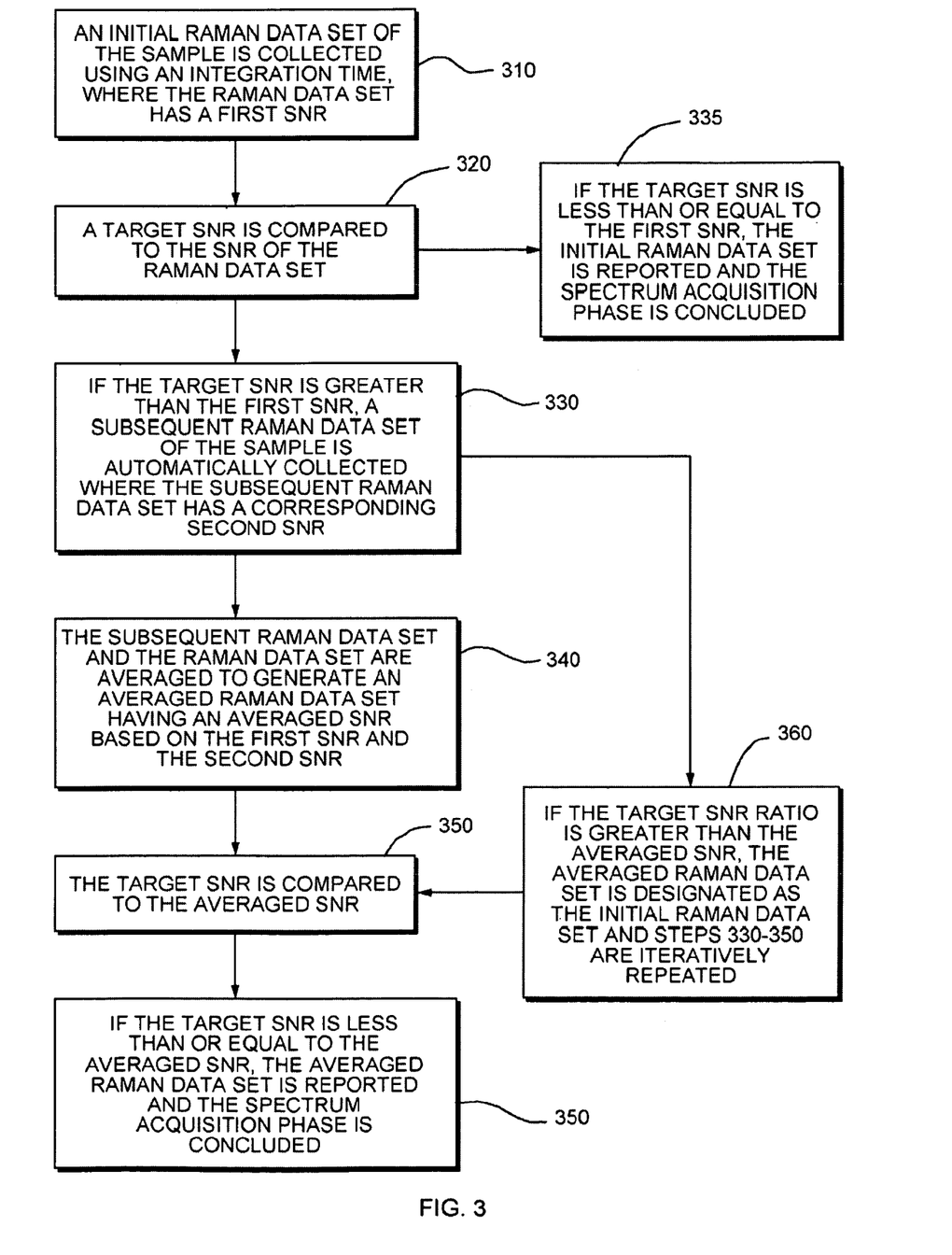
FIG. 3 is a flow diagram illustrating an exemplary method of the present disclosure.
Figures 4A, 4B:
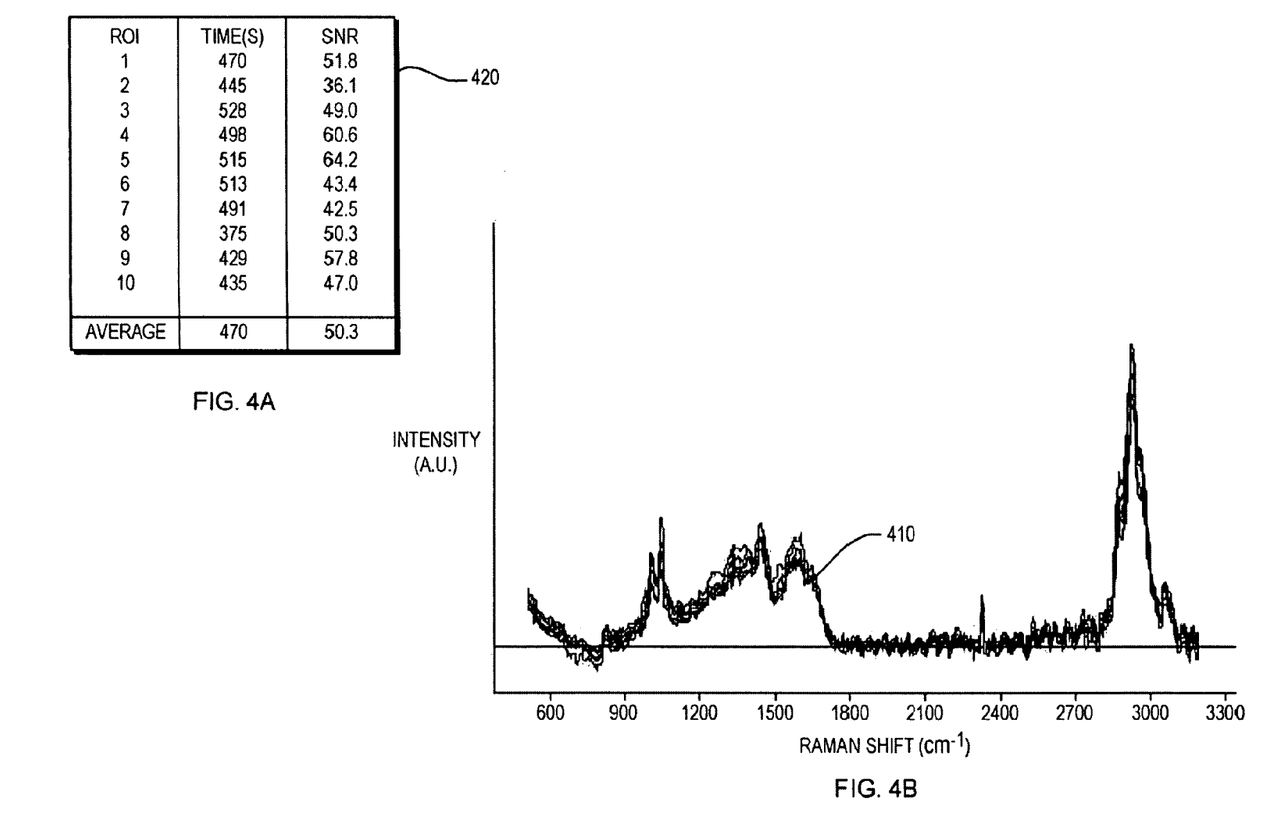
FIG. 4 illustrates a series of Raman spectra and brightfield images obtained by manual data collection techniques.
Figure 4C:
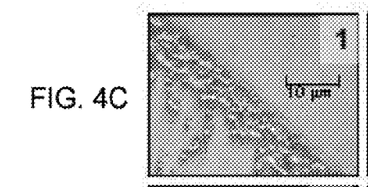
Figure 4D:
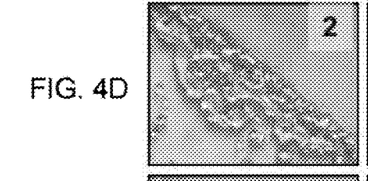
Figure 4E:
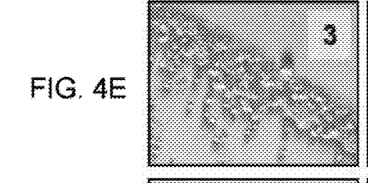
Figure 4F:
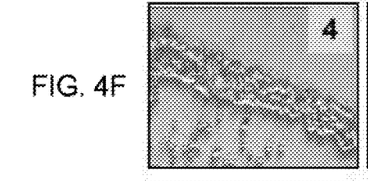
Figure 4G:
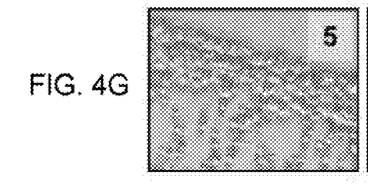
Figure 4H:
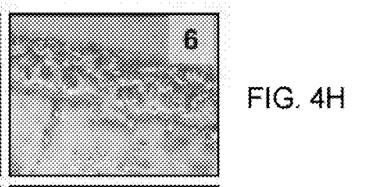
Figure 4I:
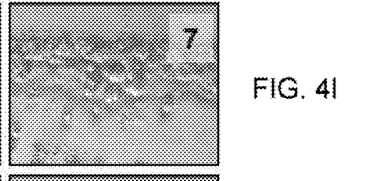
Figure 4J:
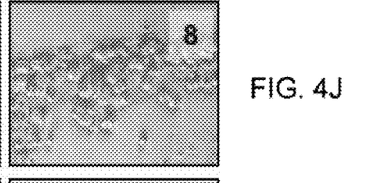
Figure 4K:
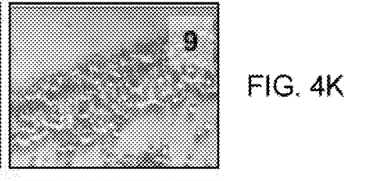
Figure 4L:
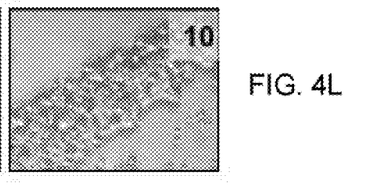
Figure 5A:
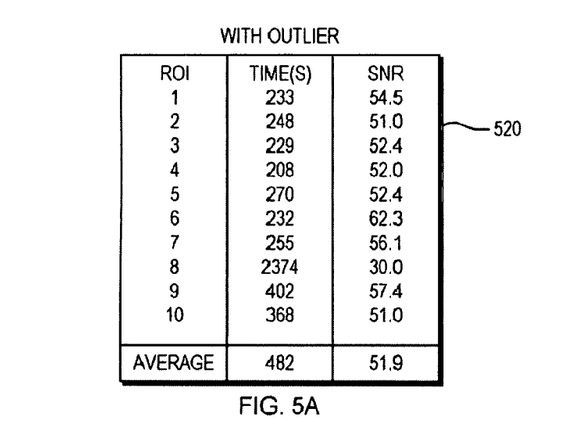
FIG. 5 illustrates a series of Raman spectra and brightfield images obtained by a method of the present disclosure.
Figure 5B:
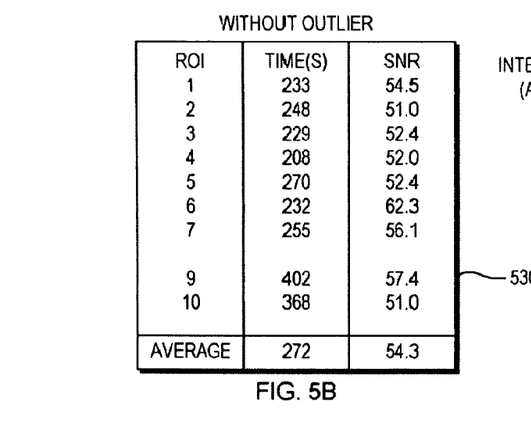
Figure 5C:
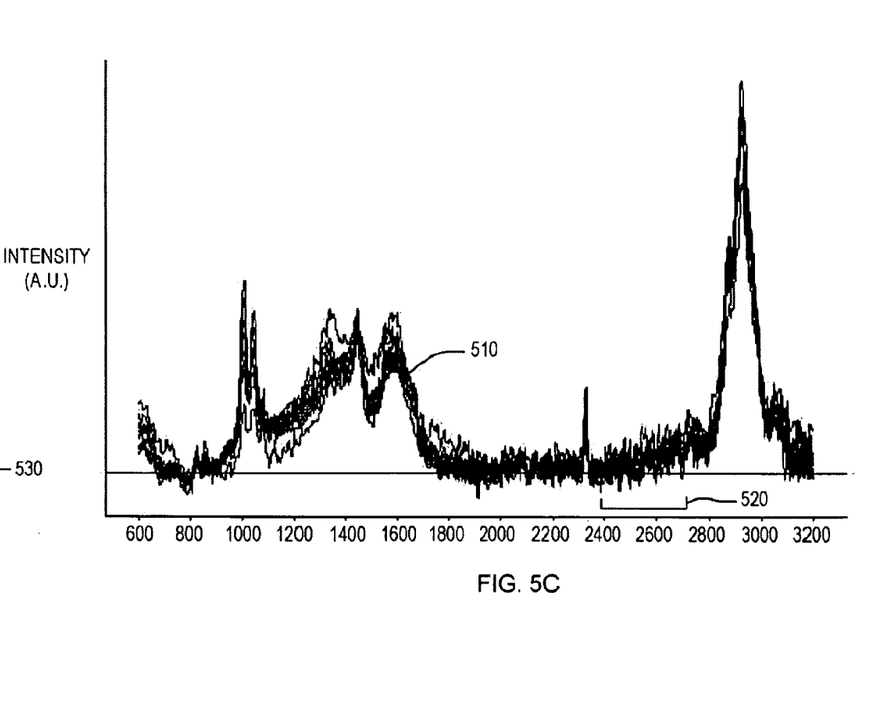
Figure 5D:
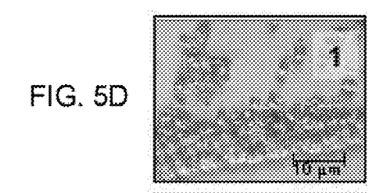
Figure 5E:
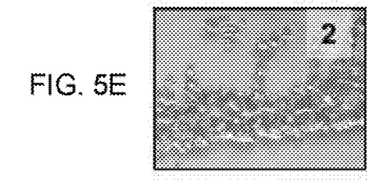
Figure 5F:
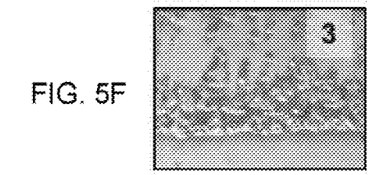
Figure 5G:
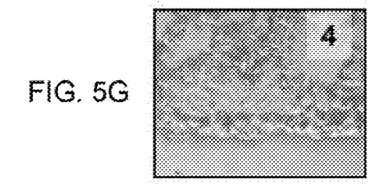
Figure 5H:
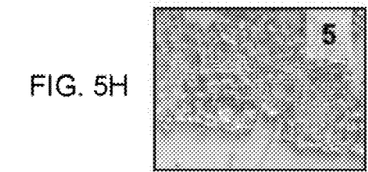
Figure 5I:
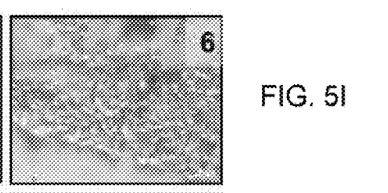
Figure 5J:
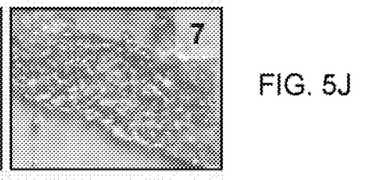
Figure 5K:
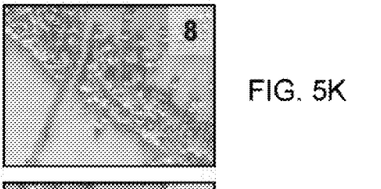
Figure 5L:
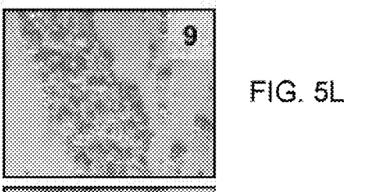
Figure 5M:
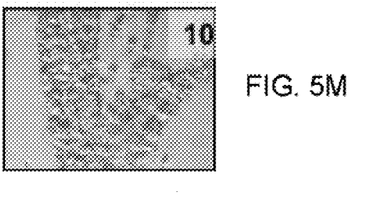

FIG. 3 is a flow chart illustrating an automated spectrum acquisition phase. In one embodiment, the method is performed in conjunction with the photobleaching phase illustrated in FIG. 2. In another embodiment, the method is performed independent of a photobleaching phase.

In step 310, a Raman data set of the sample is collected using an integration time, where the Raman data set has a corresponding signal to noise ratio ("SNR"). The Raman data set includes one or more of the following: a plurality of Raman spectra and a plurality of spatially accurate wavelength resolved Raman images. The subsequent Raman data set includes one or more of the following: a plurality of subsequent Raman spectra and a plurality of subsequent spatially accurate wavelength resolved Raman images. In one embodiment, the plurality of Raman spectra and the plurality of spatially accurate wavelength resolved Raman images may be collected by simultaneous automated acquisition of dispersive spectra and Raman images as described in U.S. Pat. No. 6,717,668 entitled "Simultaneous Imaging and Spectroscopy Apparatus" which is incorporated herein by reference in its entirety.

In an embodiment where the Raman data set includes spatially accurate wavelength resolved Raman images, the images may be collected in the same region of interest ("ROI") as was used to collect the spectral data sets acquired during the photobleaching phase.

The integration time may vary depending upon the goal of the data collection. In one embodiment where high quality spectra are desired and relatively long integration times can be tolerated, an integration time is selected which maximizes the dynamic range of the spectrometer and reduces the influence of noise attributed to electronically reading out the detector system, such as a CCD array. In another embodiment, an integration time is determined using the second background data set that is available when the relative difference between the first background data set and the second background data set is less than the threshold value. In yet another embodiment, the spectra are rapidly collecting using a short integration time ranging from 0.1 to 20 seconds or from 1 to 60 seconds for example.

With further reference to FIG. 3, a target SNR is compared to the first SNR in step 320. The SNR of the Raman data set and subsequent Raman data set are used to measure the spectral data quality to determine when to terminate the collection of Raman data sets. The SNR for each Raman data set is determined by using the corresponding maximum signal and the corresponding noise signal. The second SNR for each subsequent Raman data set is determined by using the corresponding subsequent maximum signal and the corresponding subsequent noise signal.

For the embodiment where the sequential Raman data set includes a plurality of Raman spectra, each of the spectra has a corresponding maximum signal and a corresponding noise signal. The maximum signal, for a Raman spectrum, may be obtained by a variety of approaches. In one embodiment, the integrated intensity of the maximum value of the Raman signal in the Raman spectrum is used for the maximum signal value. In another embodiment, different reference wavelength bands are used for the signal value. In yet another embodiment, the maximum signal value is based on the integrated intensity at a selected wavelength or a selected wavelength range. In still another embodiment, the maximum value of the Raman signal in the Raman data set is normalized to the intensity of the spectral band for the characteristic vibration of the Nitrogen gas molecule ($N_2$). The corresponding noise signal may include a standard deviation of spectra data points in a wavelength region of the Raman spectrum having no Raman signal which may range from 2400 $cm^{-1}$ to 2700 $cm^{-1}$.

When the Raman data set includes a plurality of spatially accurate wavelength resolved Raman images, various criteria can be used to terminate the collection of an image at a given Raman shift. In one embodiment, the signal to noise ratio is used to terminate data collection. Each image, at a give wavelength, has a corresponding noise signal selected from a background region of interest and a corresponding maximum signal selected from a signal region of interest. In this embodiment, the maximum signal is a user selected region or an automatically selected region within the image and the background region of interest is a user selected region or automatically selected region within the image. The background region of interest is different from the signal region of interest. In another embodiment, contrast within an image is used to determine when to terminate data collection.

SNR can be calculated in any given image frame by calculating the mean intensity of a region within the image frame which contains signal from the sample and dividing that mean value by the standard deviation of the intensity values within the same region within the image frame. An alternative method for calculating the signal to noise in a spatially accurate wavelength resolved image is to estimate the noise using a wavelength resolved coordinate. This can be performed using the following steps. A running average or other smooth is performed over the wavelength coordinate. The running averaged or smoothed data is then subtracted from the original data. The value at each pixel in each wavelength frame is squared and the values are summed over the wavelength coordinate to generate a single spatially accurate frame where each pixel is the sum of the squares of the difference between the original data and the smoothed data. The square root of the value at each pixel can be calculated and the value scaled using standard error estimation techniques. The result of this process is a single frame estimate of the noise along the wavelength coordinate in the spatially accurate wavelength resolved image. This image frame can be treated as an estimate of the noise. A SNR image can be generated by dividing the original data image by the noise image.

Another way to calculate SNR is to acquire an image frame at a wavelength where Raman scattered light is anticipated and acquire a second image frame at a wavelength where Raman scattered light is not anticipated. The signal can be calculated as the sum of the pixels in the first image frame, the noise can be calculated as the standard deviation of the intensity values which comprise the second image frame.

In step 330, if the target SNR is greater than the first SNR, a subsequent Raman data set of the sample is automatically collected using the integration time where the subsequent Raman data set has a corresponding second SNR. The actual values of SNR which are chosen as target values depend on the method of calculation, the instrumentation being used and the scaling factors in the data acquisition and processing systems. Typical values used in this example are in the range 10 to 100 or 10 to 1000.

In step 335, if the target SNR is less than the first SNR, the spectrum acquisition phase is concluded and the initial Raman data set is reported.

In step 340, the subsequent Raman data set and the initial Raman data set are averaged to generate an averaged Raman data set having a corresponding averaged SNR based on the first SNR and the second SNR.

In one embodiment, the spectra may be averaged using a running average of a fixed window of spectrum. For example, a five spectra running window average means averaging five Raman spectra, acquiring a subsequent Raman spectrum, discarding the first Raman spectrum of the five Raman spectra in the former average, adding the subsequent Raman spectrum and calculating a new averaged Raman data set. In another embodiment, the Raman spectrum with the lowest signal to noise ratio is replaced with a subsequent Raman spectrum and the average Raman spectrum recalculated.

In step 350, the target SNR is compared to the averaged SNR. In step 360, if the target SNR is greater than the averaged SNR, the averaged Raman data set is designated as the Raman data set and steps 330-350 are automatically repeated. If the target SNR is not reached the repetition of the steps can be stopped after a determined number of iterations. Exemplary values for the number of iterations are 5, 10, 20, and 30. In step 370, the averaged Raman data set is reported if the target SNR is less than or equal to the averaged SNR.

The method of the present disclosure also provides for the automatic adjustment of the image parameters for the plurality of spatially accurate wavelength resolved Raman images. The parameters include one or more of the following: binning or spatial resolution; integration time; spectral resolution; and laser illumination power based on a rapidly acquired low resolution Raman image. The parameter may also include the spectral range used to collect the plurality of spatially accurate wavelength resolved Raman images. In one embodiment, the plurality of spatially accurate wavelength resolved Raman images are collected over a full spectral range with automatic photobleaching if no dispersive spectrum is required. In another embodiment, the selected spectral range for the plurality of spatially accurate wavelength resolved Raman images is based on: a user's prior knowledge; the dispersive spectrum of the sample; and a rapidly acquired low spatial and or spectral resolution spatially accurate wavelength resolved image.

The method of the present disclosure also provides for the correction of instrument response during the automatic collection of the plurality of spatially accurate wavelength resolved Raman image. In this embodiment, the instrument correction may be performed by automatically acquiring a spatially accurate wavelength resolved image of a standard reference material such as the SRM 2241 developed and provided by the United States National Institute for Standards and Technology (NIST). Correction of spectral date for instrument response using such a standard can be applied to the spectral data in either or both phases of acquisition.

The method of the present disclosure also provides for an integrated auto focus step in the automatic collection of Raman spectra or spatially accurate wavelength resolved Raman images. Automated focus during acquisition is another step which can be employed to reduce the involvement of an informed, human operator and further extends the general concept of automation of spectral and spectral imaging measurements.

The method of the present disclosure also provides for the integration of automated acquisition of Raman images with various applications used to characterize a sample. These applications include composition specific particle size analysis, tissue imaging, cell imaging, complex mixture imaging, and contaminant analysis.

The method of the present disclosure also provides for automating the acquisition of a Raman image can also be performed using automated discrimination of outliers.

The method of the present disclosure also provides for the automation of various data processing steps. In one embodiment, the data processing steps includes removing of cosmic pixels. In another embodiment, the automated data processing step includes spatial filtering such as average, FFT or Gaussian blur, both of which are standard image processing steps known in the art. In another embodiment, the automated data processing step included spectral processing such as SNV, spectral smoothing, baseline correction, normalization, and mean center, all of which are tools know to those skilled in the art of spectral image analysis.

In yet another embodiment, the method of the present disclosure provides for chemometric analysis of the Raman spectral data sets. The chemometric analytical techniques include: principle component analysis, multivariate curve resolution; Euclidian distance; Cosine Correlation analysis; Mahalanobis based image segmentation; ASD based image segmentation. ASD based image segmentation is a method of segment an image based on a hyperspectral image processing approach described in the literature as Adaptive Subspace Detector. The chemometric analytical techniques may also include spectral mixture resolution which is based on predetermined spectral components or based on library search of spectra extracted from an image as described in U.S. Pat. No. 7,072,770 entitled "Method for Identifying Components of a Mixture via Spectral Analysis" which is incorporated herein by reference in its entirety.

The method of the present disclosure further provides for information visualization of the Raman data set. The visualization includes automated color overlay and automated report generation.

The methods and systems of the present disclosure are illustrated by the following examples.

EXAMPLES

Raman spectra were acquired on the ChemImage Falcon Raman Chemical Imaging Microscope™, which was equipped with a laser excitation of 532 nm. Concentrated regions of interest of *Bacillus globigii* spores were used for analysis. Samples were prepared from *Bacillus globigii* spores suspended in liquid which was spotted on aluminum coated slides for Raman analysis. Concentrated areas of *Bacillus globigii* were identified under bright field reflectance illumination and excited with the 532 nm laser, under a 100× objective.

All spectra shown in the Comparative Example, Example 1 and Example 2 were acquired and corrected for instrumental response characteristics, baseline fit and truncated. CCD bias was accounted for by subtraction of the recorded CCD signal with no laser illumination. Instrument spectral response was corrected for using National Institute of Standards and Technology (NIST) Standard Reference Material (SRM) 2242 for Raman measurements. Baseline was removed by fitting to a second order polynomial over the truncated range of the spectrum. The spectrometer was calibrated using acetaminophen standard demonstrating a spectral resolution is 4 $cm^{-1}$.

COMPARATIVE EXAMPLE

The steps for the two stages for the manual protocol are shown in Table 1. First, the photobleach phase, where the autofluorescence dissipates due to laser illumination. The second phase is the acquisition phase where a high quality spectrum is recorded after the optical response of the sample has stabilized. In the steps of each phase, an expert spectroscopist makes decisions concerning the stability of spectrum and the integration time. The integration time for photobleach interval were selected based on experience with these samples to enforce a minimal amount of time for photobleach of the sample and to ensure adequate photobleaching. Raman dispersive spectra were acquired on 10 different regions of interest.

TABLE 1

Photobleach phase

Initiate laser exposure of sample.
Acquire a spectrum at 2 minutes of laser exposure.
Repeat at 5 minutes.
Use expertise to determine when the sample is completely photobleached.
Acquisition phase TABLE 1-continued Use expertise to choose an integration time for a high quality spectrum.
Acquire a high quality spectrum.
Record the average of 5 acquisitions at the chosen integration time.

FIG. 4 shows selected Raman spectra 410 from the ROIs sampled using the manual protocol along with brightfield images of each ROI, 1-10. The table 420 shows the acquisition time and SNR of each spectrum. Time for spectral acquisition ranged between 375 and 528 seconds. The SNR for these 10 measurements ranged between 36 and 64. The mean acquisition time and mean SNR are 470 seconds and 50.3, respectively.

Example 1

FIG. 5 shows the results of automated sequential spectral acquisition for the *Bacillus globigii* spores on ROIs 1-10. The ROIs 1-10 were the same as used to obtain spectra using the manual protocol described in the Comparative Example and shown in FIG. 4. The spectra 510 of FIG. 5 were collected following the methods shown in FIGS. 2 and 3. The photobleaching phase was achieved by acquiring relatively rapid subsequent spectra approximately every second. The wavelength region of 2400 $cm^{-1}$ to 2700 $cm^{-1}$ 520 was monitored for the change in the background data set. When the relative change of the fluorescence background decrease to less than a threshold value of 1%, the photobleach phase was terminated. The integration time to collect the data sets was constrained to a maximum of 30 seconds, but for almost all of the acquisitions, the target SNR was reached before 30 seconds. The integration time ranged between 17.62 seconds and 30 seconds. The target SNR was set to a minimum of 50. For the SNR calculation, the signal was determined from the weighted area under the CH stretching envelope between 2800 $cm^{-1}$ and 3150 $cm^{-1}$. Noise was defined as the standard deviation of the signal between 2400 $cm^{-1}$ and 2700 $cm^{-1}$.

With reference to FIG. 5, the time of acquisition ranged between 208 and 2374 seconds as shown in table 520. However, this maximum time for acquisition is an extreme outlier. Excluding this outlier as shown in table 530, the mean acquisition time and mean SNR are 271 seconds and 54.3, respectively.

The extreme outlier for acquisition time was measured in ROI number 8. Note that in ROI number 8 in FIG. 5 there is a diagonal slash through the field of view. It is likely that this is some contaminant with a strong fluorescence background which happened to be in this field of view. The dynamics of the spectrum under laser exposure was not what was anticipated during the design of the automated acquisition software module in application to this type of sample and therefore the automated algorithm did not converge to the desired SNR. Absent convergence of the algorithm the acquisition was stopped after an arbitrarily chosen number (50) of spectral acquisitions which were co-averaged during the procedure. Had this chosen threshold been lower, the ultimate time period of this acquisition would have been shorter. This result does point out the importance of establishing an approach to dealing with outlier data that is consistent with automated data acquisition.

The automated spectral acquisition was 199 seconds faster than the manual protocol driven acquisition, of the Comparative Example, The final spectrum has comparable quality to that obtained in the Comparative Example. These data show automated acquisition allows non-spectroscopists to acquire high quality Raman spectra Example 3

Figure 6:
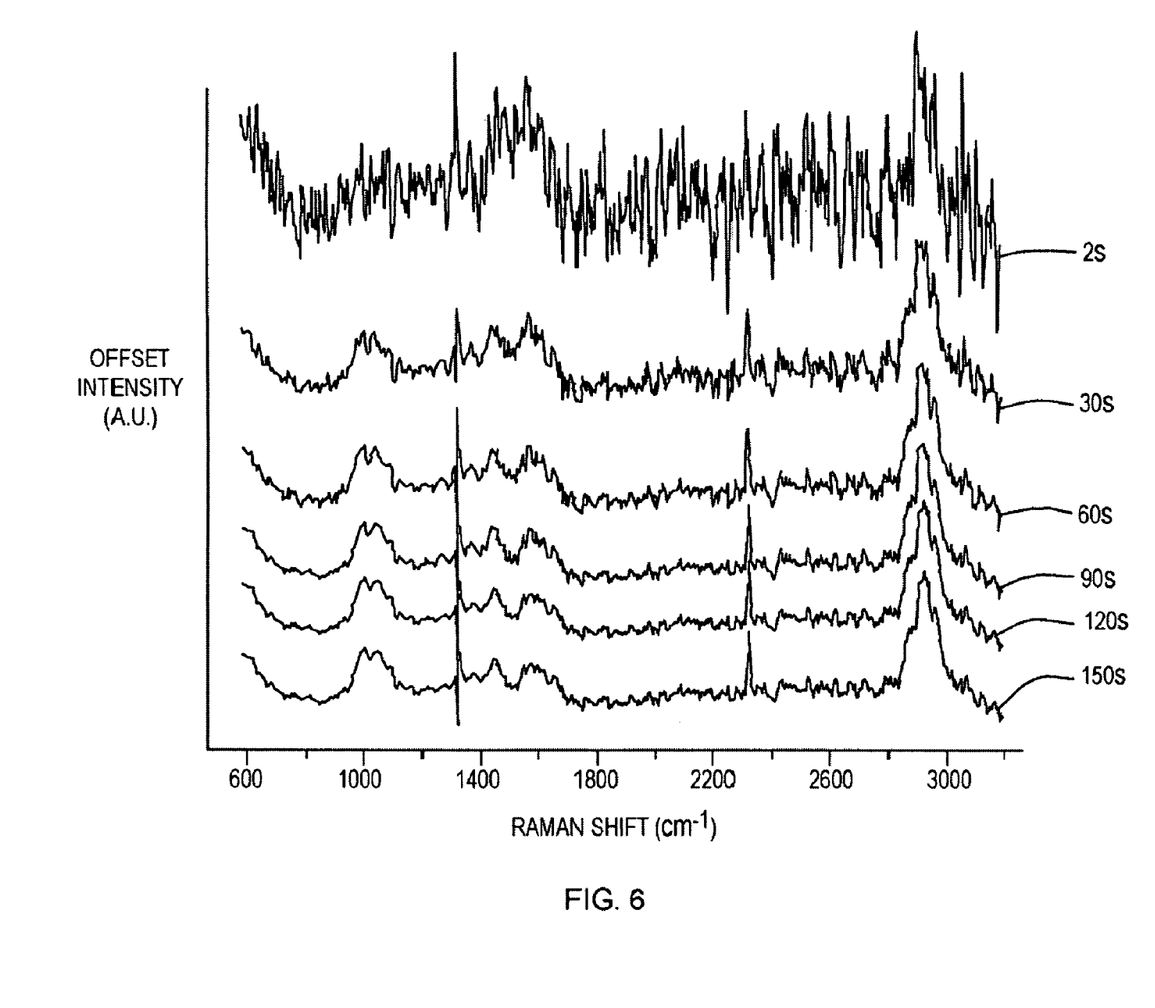
FIG. 6 illustrates a series of Raman spectra obtained by a method of the present disclosure.

In a second experiment to demonstrate rapid acquisition of a spectrum, a single particle of *Bacillus globigii* spores was isolated in the field of view of the Raman microscope. In applications where speed is critical, waiting for sample fluorescence to stabilize may not be necessary. In the area of biothreat agent, the detection and identification of organisms wittin a sample which must occur in seconds to minutes. A SNR of about 20 is required for accurate detection and identification of Bg. FIG. 6 shows mean spectra generated from signal averaging of 1, 15, 30, 45, 60 and 75 spectra. Sequential Raman spectra were acquired with a 2 second integration time for a period of 150 seconds after the initial laser illumination. This data was evaluated to estimate the SNR performance in the setting of integrated photobleaching and data collection phases. The data in FIG. 6 shows a rapid improvement in the SNR as data collection proceeds.

The present disclosure may be embodied in other specific forms without departing from the spirit or essential attributes of the disclosure. Accordingly, reference should be made to the appended claims, rather than the foregoing specification, as indicating the scope of the disclosure. Although the foregoing description is directed to the embodiments of the disclosure, it is noted that other variations and modification will be apparent to those skilled in the art, and may be made without departing from the spirit or scope of the disclosure.

What is claimed is:

1. A method comprising the following steps being performed automatically:
   a) collecting a spectral data set of a sample, said spectral data set having a corresponding first background data set;
   b) collecting a subsequent spectral data set of said sample, said subsequent spectral data set having a corresponding second background data set;
   c) determining a relative difference between said first and said second background data sets;
   d) comparing a threshold value to said relative difference;
   e) designating the second background data set as the first background data set and iteratively repeating steps (b)-(d) until said relative difference is less than said threshold value; and
   f) using, as part of a spectrum acquisition phase for said sample, said second background data set that is available when said relative difference becomes less than said threshold value.

2. The method of claim 1, wherein said spectrum acquisition phase comprises performing the following steps automatically:
   g) collecting an initial Raman data set of said sample using an integration time calculated from said second background data set that is available when said relative difference becomes less than said threshold value, said initial Raman data set having a corresponding first signal to noise ratio (SNR);
   h) comparing a target SNR to said first SNR;
   i) if said target SNR is less than said first SNR, indicating conclusion of said spectrum acquisition phase by reporting said initial Raman data set;
   j) if said target SNR is greater than said first SNR, collecting a subsequent Raman data set of said sample using said integration time, said subsequent Raman data set having a corresponding second SNR;
   k) averaging the subsequent Raman data set and the initial Raman data set to generate an averaged Raman data set having a corresponding averaged SNR based on said first SNR and said second SNR;
   l) comparing the target SNR to said averaged SNR;
   m) if said target SNR is greater than said averaged SNR, designating the averaged Raman data set as the initial Raman data set and iteratively repeating steps (j)-(l); and
   n) if said target SNR is less than or equal to said averaged SNR, indicating conclusion of said spectrum acquisition phase by reporting the averaged Raman data set.

3. The method of claim 1, wherein said first background data set comprises a wavelength region ranging from 2400 $cm^{-1}$ to 2700 $cm^{-1}$ of a spectrum, and wherein said second background data set comprises a wavelength region ranging from 2400 $cm^{-1}$ to 2700 $cm^{-1}$ of a subsequent spectrum.

4. The method of claim 1, wherein said first background data set comprises a background region of interest in a first spatially accurate wavelength resolved image and wherein said second background data set comprises a subsequent background region of interest in a second spatially accurate wavelength resolved image.

5. The method of claim 4, wherein said first spatially accurate wavelength resolved image occurs at a wavelength ranging from 2400 $cm^{-1}$ to 2700 $cm^{-1}$ and wherein said second spatially accurate wavelength resolved image occurs at a wavelength ranging from 2400 $cm^{-1}$ to 2700 $cm^{-1}$.

6. The method of claim 1, wherein said spectral data set and said subsequent spectral data set are automatically collected at a time interval of less than 5 seconds.

7. The method of claim 1, wherein said threshold value is selected from a range of values between 0 and 5 percent.

8. The method of claim 2, wherein said initial Raman data set includes one or more of the following: a plurality of Raman spectra, and a plurality of spatially accurate wavelength resolved Raman images; and wherein said subsequent Raman data set includes one or more of the following: a plurality of subsequent Raman spectra, and a plurality of subsequent spatially accurate wavelength resolved Raman images.

9. The method of claim 8, wherein each of said plurality of Raman spectra has a corresponding maximum signal and a corresponding noise signal, and wherein each of said plurality of subsequent Raman spectra has a corresponding subsequent maximum signal and a corresponding subsequent noise signal.

10. The method of claim 9, further comprising performing the following steps automatically:
    o) determining said first SNR using said corresponding maximum signal and said corresponding noise signal; and
    p) determining said second SNR using said corresponding subsequent maximum signal and said corresponding subsequent noise signal.

11. The method of claim 9, wherein said corresponding noise signal comprises a first standard deviation of spectral data points in a wavelength region of the respective Raman spectrum having no Raman signal, and wherein said corresponding subsequent noise signal comprises a second standard deviation of spectral data points in a wavelength region of the respective subsequent Raman spectrum having no Raman signal.

12. The method of claim 9, wherein said wavelength region of the Raman spectrum having no Raman signal ranges from 2400 $cm^{-1}$ to 2700 $cm^{-1}$, and wherein said wavelength region of the subsequent Raman spectrum having no Raman signal ranges from 2400 cm$^{-1}$ to 2700 cm$^{-1}$.

13. The method of claim 8, wherein each of said plurality of spatially accurate wavelength resolved Raman images has a corresponding noise signal selected from a background region of interest and a corresponding maximum signal selected from a signal region of interest, and wherein each of said plurality of subsequent spatially accurate wavelength resolved Raman images has a corresponding subsequent noise signal selected from a subsequent background region of interest and a corresponding subsequent maximum signal selected from a subsequent signal region of interest.

14. The method of claim 13, further comprising performing the following steps automatically:
  o) determining said first SNR using said corresponding maximum signal and said corresponding noise signal; and
  p) determining said second SNR using said corresponding subsequent maximum signal and said corresponding subsequent noise signal.

15. A system comprising:
  a spectroscopic device;
  an imaging device;
  a machine readable program code containing executable program instructions; and
  a processor operatively coupled to said spectroscopic device and said imaging device and configured to execute said machine readable program code so as to automatically perform the following:
    a) configure said spectroscopic device to perform the following:
      1) collect a spectral data set of a sample, said spectral data set having a corresponding first background data set;
      2) collect a subsequent spectral data set of said sample, said subsequent spectral data set having a corresponding second background data set;
    b) determine a relative difference between said first and said second background data sets;
    c) compare a threshold value to said relative difference;
    d) designate the second background data set as the first background data set and iteratively repeating steps (a)(2)-(c) until said relative difference is less than said threshold value; and
    e) use, as part of a spectrum acquisition phase for said sample, said second background data set that is available when said relative difference becomes less than said threshold value.

16. The system of claim 15, wherein said processor further configured to automatically perform the following:
  f) configure said spectroscopic device to collect an initial Raman data set of said sample using an integration time calculated from said second background data set that is available when said relative difference becomes less than said threshold value, said initial Raman data set having a corresponding first signal to noise ratio (SNR);
  g) compare a target SNR to said first SNR;
  h) if said target SNR is less than said first SNR, indicate conclusion of said spectrum acquisition phase by reporting said initial Raman data set;
  i) if said target SNR is greater than said first SNR, configure said spectroscopic device to collect a subsequent Raman data set of said sample using said integration time, said subsequent Raman data set having a corresponding second SNR;
  j) average the subsequent Raman data set and the initial Raman data set to generate an averaged Raman data set having a corresponding averaged SNR based on said first SNR and said second SNR;
  k) compare the target SNR to said averaged SNR;
  l) if said target SNR is greater than said averaged SNR, designate the averaged Raman data set as the initial Raman data set and iteratively repeat steps (i)-(k); and
  m) if said target SNR is less than or equal to said averaged SNR indicate conclusion of said spectrum acquisition phase by reporting the averaged Raman data set.

17. A storage medium containing machine readable program code, which, when executed by a processor, causes said processor to automatically perform the following:
  a) configure a spectroscopic device to perform the following:
    1) collect a spectral data set of a sample, said spectral data set having a corresponding first background data set;
    2) collect a subsequent spectral data set of said sample, said subsequent spectral data set having a corresponding second background data set;
  b) determine a relative difference between said first and said second background data sets;
  c) compare a threshold value to said relative difference;
  d) designate the second background data set as the first background data set and iteratively repeating steps (a) (2)-(c) until said relative difference is less than said threshold value; and
  e) use, as part of a spectrum acquisition phase for said sample, said second background data set that is available when said relative difference becomes less than said threshold value.

18. The storage medium of claim 17, wherein said machine readable program code, when executed by said processor, causes said processor to further automatically perform the following:
  f) configure said spectroscopic device to collect an initial Raman data set of said sample using an integration time calculated from said second background data set that is available when said relative difference becomes less than said threshold value, said initial Raman data set having a corresponding first signal to noise ratio (SNR);
  g) compare a target SNR to said first SNR;
  h) if said target SNR is less than said first SNR, indicate conclusion of said spectrum acquisition phase by reporting said initial Raman data set;
  i) if said target SNR is greater than said first SNR, configure said spectroscopic device to collect a subsequent Raman data set of said sample using said integration time, said subsequent Raman data set having a corresponding second SNR;
  j) average the subsequent Raman data set and the initial Raman data set to generate an averaged Raman data set having a corresponding averaged SNR based on said first SNR and said second SNR;
  k) compare the target SNR to said averaged SNR;
  l) if said target SNR is greater than said averaged SNR, designate the averaged Raman data set as the initial Raman data set and iteratively repeat steps (i)-(k); and
  n) if said target SNR is less than or equal to said averaged SNR indicate conclusion of said spectrum acquisition phase by reporting the averaged Raman data set.

19. A system comprising:
  means to collect one or more of the following: a spectral data set of a sample and a Raman data set of said sample;

means to image one or more of the following: a spatially accurate wavelength resolved image of said sample and a spatially accurate wavelength resolved Raman image of said sample;

means to execute instructions to automatically perform the following:
  a) collect a spectral data set of a sample, said spectral data set having a corresponding first background data set;
  b) collect a subsequent spectral data set of said sample, said subsequent spectral data set having a corresponding second background data set;
  c) determine a relative difference between said first and said second background data sets;
  d) compare a threshold value to said relative difference;
  e) designate the second background data set as the first background data set and iteratively repeating steps (b)-(d) until said relative difference is less than said threshold value; and
  f) use, as part of a spectrum acquisition phase for said sample, said second background data set that is available when said relative difference becomes less than said threshold value.

20. The system of claim 19, further comprising:
means to execute further instructions to automatically perform the following
  g) collect an initial Raman data set of said sample using an integration time calculated from said second background data set that is available when said relative difference becomes less than said threshold value, said initial Raman data set having a corresponding first signal to noise ratio (SNR);
  h) compare a target SNR to said first SNR;
  i) if said target SNR is less than said first SNR, indicate conclusion of said spectrum acquisition phase by reporting said initial Raman data set;
  j) if said target SNR is greater than said first SNR, collect a subsequent Raman data set of said sample using said integration time, said subsequent Raman data set having a corresponding second SNR;
  k) average the subsequent Raman data set and the initial Raman data set to generate an averaged Raman data set having a corresponding averaged SNR based on said first SNR and said second SNR;
  l) compare the target SNR to said averaged SNR;
  m) if said target SNR is greater than said averaged SNR, designate the averaged Raman data set as the initial Raman data set and iteratively repeat steps (j)-(l); and
  n) if said target SNR is less than or equal to said averaged SNR indicate conclusion of said spectrum acquisition phase by reporting the averaged Raman data set.

21. A method comprising performing the following steps automatically:
  a) collecting an initial Raman data set of a sample using an integration time comprising one or more of the following: an integration time ranging from 0.1 to 20 seconds and an integration time ranging from 1 to 60 seconds, said initial Raman data set having a corresponding first signal to noise ratio (SNR);
  b) comparing a target SNR to said first SNR;
  c) if said target SNR is less than said first SNR, indicating conclusion of a spectrum acquisition phase by reporting said initial Raman data set;
  d) if said target SNR is greater than said first SNR, collecting a subsequent Raman data set of said sample using said integration time, said subsequent Raman data set having a corresponding second SNR;
  e) averaging the subsequent Raman data set and the initial Raman data set to generate an averaged Raman data set having a corresponding averaged SNR based on said first SNR and said second SNR;
  f) comparing the target SNR to said averaged SNR;
  g) if said target SNR is greater than said averaged SNR, designating the averaged Raman data set as the initial Raman data set and iteratively repeating steps (d)-(f); and
  h) if said target SNR is less than or equal to said averaged SNR indicating conclusion of said spectrum acquisition phase by reporting the averaged Raman data set.

22. The method of claim 21, wherein said initial Raman data set includes one or more of the following: a plurality of Raman spectra, and a plurality of spatially accurate wavelength resolved Raman images; and wherein said subsequent Raman data set includes one or more of the following: a plurality of subsequent Raman spectra, and a plurality of subsequent spatially accurate wavelength resolved Raman images.

23. The method of claim 22, wherein each of said plurality of Raman spectra has a corresponding maximum signal and a corresponding noise signal, and wherein each of said plurality of subsequent Raman spectra has a corresponding subsequent maximum signal and a corresponding subsequent noise signal.

24. The method of claim 23, further comprising performing the following steps automatically:
  i) determining said first SNR using said corresponding maximum signal and said corresponding noise signal; and
  j) determining said second SNR using said corresponding subsequent maximum signal and said corresponding subsequent noise signal.

25. The method of claim 23, wherein said corresponding noise signal comprises a first standard deviation of spectral data points in a wavelength region of the respective Raman spectrum having no Raman signal, and wherein said corresponding subsequent noise signal comprises a second standard deviation of spectral data points in a wavelength region of the respective subsequent Raman spectrum having no Raman signal.

26. The method of claim 25, wherein said wavelength region of the Raman spectrum having no Raman signal ranges from 2400 $cm^{-1}$ to 2700 $cm^{-1}$, and wherein said wavelength region of the subsequent Raman spectrum having no Raman signal ranges from 2400 $cm^{-1}$ to 2700 $cm^{-1}$.

27. The method of claim 26, wherein each of said plurality of spatially accurate wavelength resolved Raman images has a corresponding noise signal selected from a background region of interest and a corresponding maximum signal selected from a signal region of interest, and wherein each of said plurality of subsequent spatially accurate wavelength resolved Raman images has a corresponding subsequent noise signal selected from a subsequent background region of interest and a corresponding subsequent maximum signal selected from a subsequent signal region of interest.

28. The method of claim 27, further comprising performing the following steps automatically:
  o) determining said first SNR using said corresponding maximum signal and said corresponding noise signal; and
  p) determining said second SNR using said corresponding subsequent maximum signal and said corresponding subsequent noise signal.

* * * * *